US010154899B1

(12) United States Patent
Biggs et al.

(10) Patent No.: US 10,154,899 B1
(45) Date of Patent: Dec. 18, 2018

(54) AUTOMATIC VARIABLE FREQUENCY ELECTROLARYNX

(71) Applicant: Archer Medical Devices LLC, Lexington, KY (US)

(72) Inventors: Michael Biggs, Los Angeles, CA (US); Matthew Griffin, Lexington, KY (US)

( * ) Notice: Subject to any disclaimer, the term of this patent is extended or adjusted under 35 U.S.C. 154(b) by 0 days.

(21) Appl. No.: 15/594,206

(22) Filed: May 12, 2017

Related U.S. Application Data

(60) Provisional application No. 62/335,135, filed on May 12, 2016.

(51) Int. Cl.
*A61F 2/20* (2006.01)
*G10L 13/02* (2013.01)
*G10L 21/02* (2013.01)

(52) U.S. Cl.
CPC ............ *A61F 2/20* (2013.01); *G10L 13/02* (2013.01); *A61F 2002/206* (2013.01); *G10L 21/02* (2013.01)

(58) Field of Classification Search
CPC ...... A61F 2/20; A61F 2002/206; G10L 13/02; G10L 21/02
See application file for complete search history.

(56) References Cited

U.S. PATENT DOCUMENTS

| 4,028,492 A | 6/1977 | Sickel | |
| 5,095,798 A * | 3/1992 | Okada | A63F 13/00 |
| | | | 381/17 |
| 5,326,349 A * | 7/1994 | Baraff | A61F 2/20 |
| | | | 381/70 |
| 5,812,681 A | 9/1998 | Griffin | |
| 6,252,966 B1 | 6/2001 | Griffin | |
| 6,310,556 B1 * | 10/2001 | Green | G08B 21/185 |
| | | | 340/539.1 |
| 6,795,807 B1 | 9/2004 | Baraff | |
| 7,212,639 B1 | 5/2007 | Houston | |
| 8,103,012 B2 | 1/2012 | Kuper | |
| 9,031,249 B1 | 5/2015 | Griffin | |

(Continued)

FOREIGN PATENT DOCUMENTS

| JP | 2008242234 A * | 10/2008 |
| WO | WO2003013395 A1 | 2/2003 |
| WO | WO2007113056 A1 | 10/2007 |

OTHER PUBLICATIONS

Shakya et al., "Development of an Electrolarynx Capable of Supporting Tonal Distinctions in Madarin." Trinity College Symposium Poster, date unknown.

(Continued)

*Primary Examiner* — Sonia L Gay
(74) *Attorney, Agent, or Firm* — Michael Coblenz

(57) ABSTRACT

A automatic variable frequency electrolarynx with a microcontroller that generates a random but controlled frequency that creates a random tone. The controlled random tone allows the user of the electrolarynx to use the device without the monotone of standard electrolarynx. The electrolarynx also includes an encoder that allows the user to easily adjust the base tone of the device. The electrolarynx also includes an integrated LED light in the on/off switch to indicate whether the encoder is in volume control or tone control mode. The microcontroller also conducts an automatic power source check, and produces a musical tone when the battery is low.

35 Claims, 4 Drawing Sheets

(56) References Cited

U.S. PATENT DOCUMENTS

| | | |
|---|---|---|
| 9,561,099 B1 | 2/2017 | Griffin et al. |
| 9,578,405 B2 | 2/2017 | Sun et al. |
| 2003/0031326 A1 | 2/2003 | Lukacovic |
| 2009/0060226 A1* | 3/2009 | Chen ........................ H04R 3/00 381/107 |
| 2009/0139847 A1* | 6/2009 | Yoon ..................... D06F 39/005 200/5 A |
| 2013/0107438 A1* | 5/2013 | Lee ........................ G06F 3/0221 361/679.08 |
| 2013/0294613 A1* | 11/2013 | Nagel ....................... A61F 2/20 381/70 |

OTHER PUBLICATIONS

TruTone Electrolarynx product brochure, 2013.

* cited by examiner

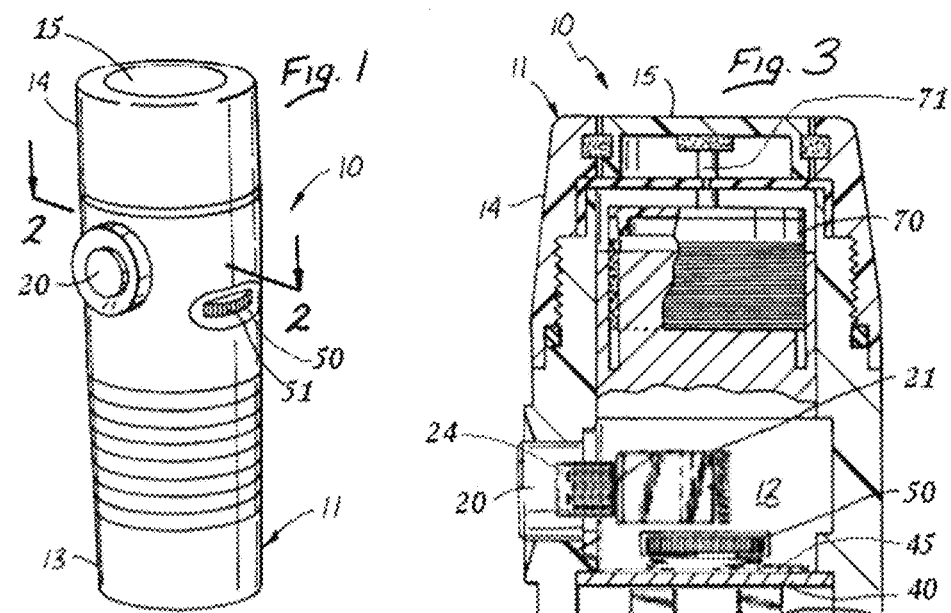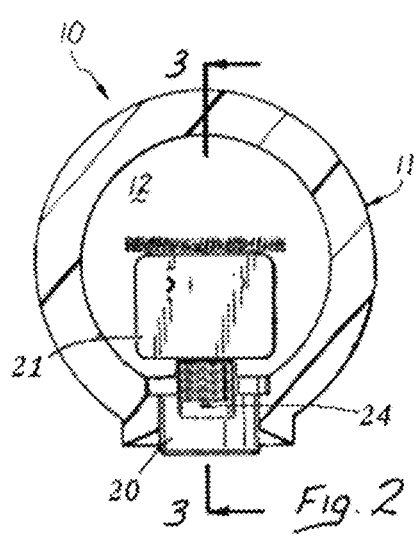

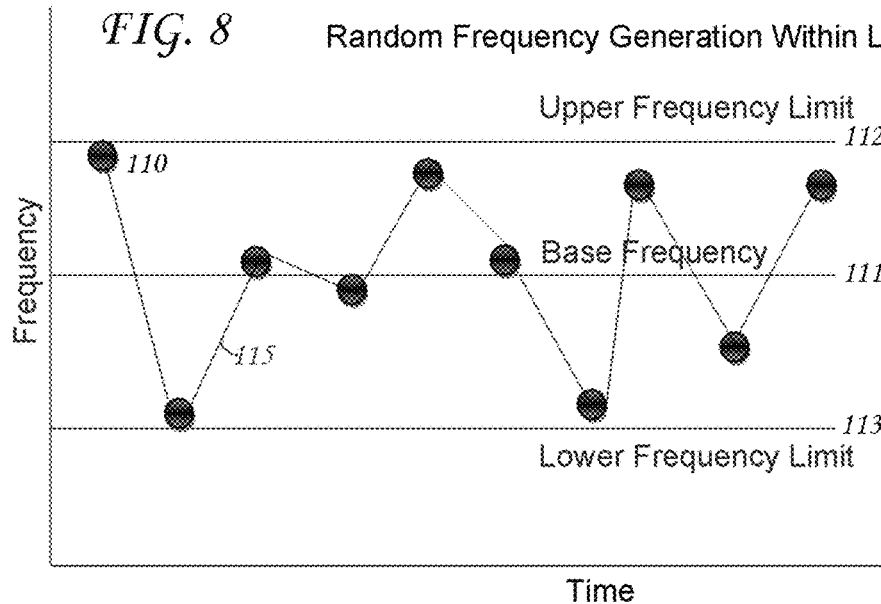
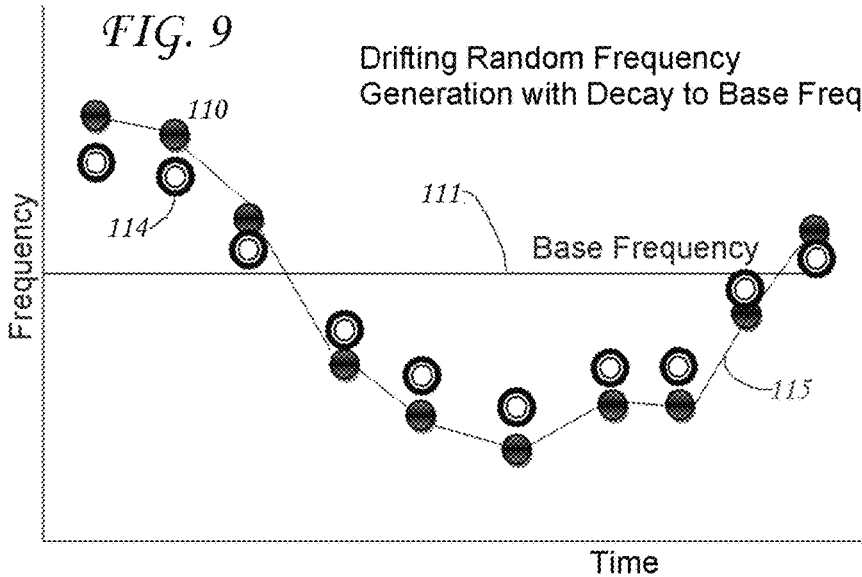

AUTOMATIC VARIABLE FREQUENCY ELECTROLARYNX

CROSS REFERENCE TO RELATED APPLICATIONS

This application claims priority to U.S. provisional application Ser. No. 62/335,135, filed on May 12, 2016, and incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to an artificial electronic larynx, often called an electrolarynx, which is a device used to facilitate speech in people without vocal cords. More specifically the invention relates to a means for altering the tone of the electrolarynx to reduce the monotone sound and create more natural sounding voice.

Description of the Related Art

People can have their larynx or vocal chords removed due to a number of medical issues such as laryngeal cancer. When the individual has the larynx removed they lose the ability to create normal speech. The artificial larynx is a vibrator that is pressed against an area of the throat near where the larynx once was. It produces the vibration formally produced by the larynx, which allows the user to form words through the mouth. A typical electrolarynx uses a transducer to generate a buzzing noise. One of the main drawbacks for standard electrolarynx is that the standard transducer creates a buzz in a single tone. While this allows the user to create understandable words, the speech is in a monotone and hence has a robotic sound.

The human voice functions in a range of between about 80 Hz to about 300 Hz, with most men having a typically lower tone voice of between 85 Hz to about 185 Hz, and most women's voices in the range of between about 160 Hz and about 255 Hz. The human ear can hear in a range of between about 20 Hz and about 20,000 Hz, with the low end being a deep, base sound, and the higher end being high and near a sharp whistle. This is far outside of the range of the human voice. Audible sound is defined by its frequency in Hertz, or cycles per second. A low sound, like the sound of a bull frog or base guitar, vibrates near the low range of a audible spectrum, and a high sound, like the buzz of a mosquito or a high note on a flute, operates at the high range.

An electrolarynx produces a vibration that replaces the vibration of the human larynx. Most electrolarynx use a transducer, which is typically an electromagnetic bobbin that vibrates back and forth based on the electric current run through the electromagnet. The bobbin typically has a small plunger that hits against a diaphragm, or thin plastic covering at the end of the electrolarynx, and it is this tapping that creates the vibration. Each cycle of the transducer is the time between the strike of the plunger. The tone of the transducer, therefore, is controlled by the frequency of the transducer. A low tone will have a slower vibration rate, and a higher tone will have a faster vibration rate. Men typically have a lower tone than women, and the ability to control the tone of the electrolarynx allows the same device to be used for both men and women.

The human voice varies in tone, volume, and inflection (emphasis on syllables based on both tone and volume) during normal speech. Normal human speech is highly variable even during a short sentence. This is partly due to the fact that vowels generally have a lower frequency than consonants. But the tone (and the volume) also changes based on excitement or stress levels or due to the speaker changing tone (or volume) for emphasis. This means that there is a certain amount of randomness in typical human speech. Standard electrolarynx, with a single frequency or tone, sound particularly monotone or robotic because the human ear is attuned to the speech patterns of the normal voice.

There are a number of prior art patents that attempt to alter the tone and volume of the vibration to create a more natural sounding voice. Several electro larynx devices on the market use manual or automatic means to address the robotic quality of monotone speech. These methods include: (1) user determined tone changes through the use of a potentiometer or pressure sensitive resistor; (2) Dual activation buttons with differing tones; and (3) automatic pre-determined and stepped pitch change during use in an attempt to mimic vocal patterns. While these do improve the monotone, there are a number of disadvantages to these methods. First, many of these devices require the user to constantly change the tone or volume settings to reduce the monotone, which means the user has learn how to use the device and how to manipulate the controls during use. This requires user training and acquired skill in order to control tone changes. Another common problem with these devices is that tone changes may be set in such a wide band, from low deep bass to high soprano pitch, that user control becomes difficult. Dual button tone change systems also require active user participation, and dual tones, while an improvement, are still insufficient since natural voices usually have more than two tones. The use of predetermined vocal patterns, which are set from prerecorded voices, are also an improvement, but one drawback is that vocal patters differ by region and from person to person so that the set pattern could be out of sync with the actual sentence being spoken.

U.S. Pat. No. 5,326,349, to Baraff, discloses a small speaker unit placed in the mouth which is controlled by an external hand held device. The '349 uses a preset waveform (i.e. not random) to alter the tone, but it also includes a "random delay variable" which interjects gaps in the sound with a vary small amount of random frequency variation to make the speech sound somewhat less robotic and more natural. These small frequency changes in the gaps between the sound are random, but tone change in the voice itself is not random. The computer software program is stored on a removable chip which is interchanged with other chips incorporating tone generating programs to allow different voice tones depending upon user preferences. U.S. Pat. No. 6,795,807, also to Baraff, discloses a speech aid device that includes a receptor and microphone warn against the neck. The device includes software that is designed to attempt to mimic natural human speech. This is achieved altering the pitch (or tone) based on the previous tone. A preset calculation takes the tone and alters it to create the next tone. This results in an automatic alteration of the tone of the speech, but based on a non-random or pre-set pattern.

U.S. Pat. No. 5,812,681, to Griffin (not the current applicant) discloses a means for altering the tone of the electrolarynx. The tone of this electrolarynx is altered by means of a push-button pressure sensitive controller that allows the user to vary the frequency of the tone. While this is an improvement over the standard monotone electrolarynx, one drawback is that it requires training for the use, and requires active involvement of the user, which is often difficult to accomplish. U.S. Pat. No. 9,561,099, also to Griffin is an electrolarynx that has an incorporated pressure-sensitive resistor (PSR) that can be used to alter the frequency of the vibration and hence the tone of the electrolarynx. The user can adjust the tone of the electrolarynx based on how hard they press the PSR. This allows adjustment of the tone, but requires active user input and training.

U.S. Pat. No. 7,212,639, to Houston, describes the use of glottal sampling to produce a repeatable tonal pattern that is used with a neck-type electro-larynx device. Essentially vocal information is taken from a recording of the user, or of a person with a similar voice, and this provides an altered tone generator. The tone varies, but is not purely random. While this is an improvement over the prior art monotone devices, one drawback is that it requires sampling from the users recorded speech or the speech of a person with a similar voice. This adds a level of complexity and a time component that that can add time, money, and complexity. U.S. Patent Application, Publication No. 2013/0294613, to Nagel, includes a capacitive sensor that allows the user to adjust the frequency (or tone) of the device during use. Each of these prior art references discloses different ways to adjust the tone of the electrolarynx. The teachings of each as they relate to the human voice and the use and operation of electrolarynx are incorporated herein.

Despite the improvements presented by these inventions, there is still a need for an electrolarynx that produces a non-monotone voice and hence produces a more natural sounding speech pattern for the user of the electrolarynx, but one that is easily adjusted and simple to use.

SUMMARY OF THE INVENTION

This invention is an improved electrolarynx with features that improve the sound of the user's voice to make it more natural sounding. This comprises a computer chip, or microcontroller, that creates a semi-random variation in the tone to mimic the natural variations in human speech, which are random. The microcontroller sends a signal to the transducer to vibrate as a pre-determined frequency, which is heard by the ear as a tone. The microcontroller produce a frequency that varies within a set range around a pre-determined base frequency. This variation is a function of the original frequency, with a variable change, but with a delay constant that brings the frequency back towards the base frequency. This creates a random, drifting, frequency, but one that is constrained near the preset base frequency. This creates random variations in the tone of the electrolarynx, and a less monotone sounding voice for the user of the electrolarynx.

The invention also includes a number of features that make it easier and more convenient to use. These include a multi-function thumb-wheel encoder that controls both the volume and the tone of the electro-larynx, which makes it easier for the user to operate the device. There are also features that improve the functionality of the invention. These include; a "false turn-on" prevention feature that prevents the device from being turned on by a single brief press of the power button; a low battery warning tone generated through the tone generator control, an LED light in the power switch that indicates the status of the device; an audible warning for the minimum voltage settings (the audible "musical tune" warning is a low battery indicator); and a variable "power on" cycle that can reduce adjustments based on the volume setting.

BRIEF DESCRIPTION OF THE DRAWINGS

FIG. 1 is a perspective view of the electrolarynx.

FIG. 2 is a horizontal cross-section view of the invention

FIG. 3 is a vertical cross-section view of the interior of the invention.

FIG. 4 is a detailed view of the multi-function thumb wheel encoder.

FIG. 8 is a graph of a purely random tone generation.

FIG. 9 is a graph of the pseudorandom tone generation of the present invention.

DETAILED DESCRIPTION OF THE INVENTION

Figure 5:
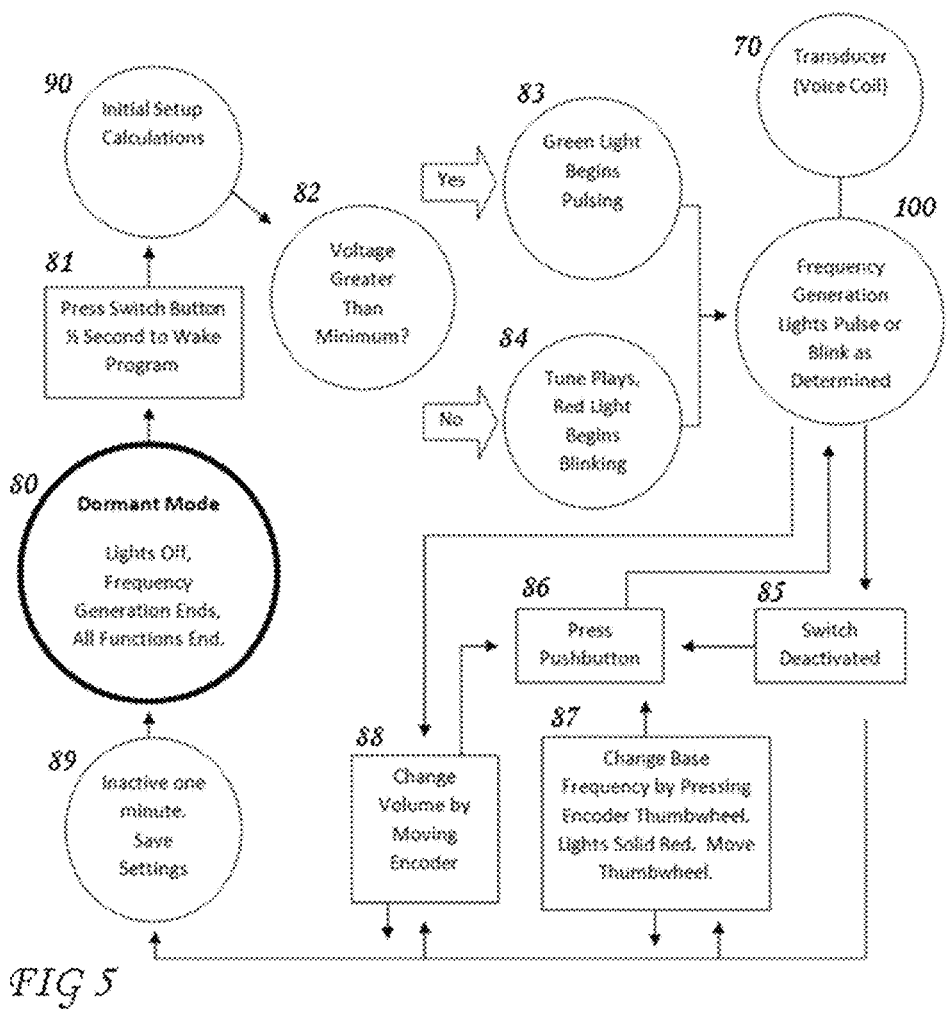
FIG. 5 is a flow chart of the operational mode of the microcontroller.

Detailed embodiments of the present invention are disclosed herein. It is to be understood that the disclosed embodiments are merely exemplary of the invention, and that there may be a variety of other alternate embodiments. The figures are not necessarily to scale, and some features may be exaggerated or minimized to show details of particular components. Therefore, specified structural and functional details disclosed herein are not to be interpreted as limiting, but merely as a basis for teaching one skilled in the art to employ the varying embodiments of the present invention.

FIG. 1 is an external view of the electrolarynx 10 showing the visible components of the device. FIG. 2 is a horizontal cut-away cross-section of the electrolarynx 10 showing some of the control circuitry, and FIG. 3 is a vertical cut-away cross-section of the electrolarynx 10 showing the main internal components of the device. Generally, the electrolarynx 10 includes a housing 11 that extends along a central axis of elongation 12 between a bottom end cap 13 at a bottom end portion of the housing 11, and a top end cap 14 at a forward end portion of the housing 11. The user grasps the housing 11, presses the top end cap 14 (which contains the vibrating sound-producing transducer 70 portion at the forward end of the electrolarynx 10) against the outside of their throat, and presses the pushbutton 20 to activate the transducer and create the vibrating tone. The vibrating tone of the electrolarynx 10 travels through the neck and into the mouth where the user then modulates the sound by making the usual tongue, teeth, and lip constrictions so as to articulate the modulated tone of human speech.

The transducer 70 creates a buzzing sound at a frequency determined by the microcontroller 45. The transducer creates the buzzing sound with a small plunger 71 that taps rapidly against a diaphragm 15, or thin plastic covering at the top end cap 14 of the electrolarynx 10. The plunger taps so fast that it sounds like a buzz. The frequency is the speed at which the plunger taps against the diaphragm 15, and the buzzing sound is heard audibly as a pitch or tone. The higher the frequency, or the faster the buzz, the higher the tone. Conversely the lower the frequency the slower the buzz and the lower the tone. Audible tones are measured in Hertz (Hz), or cycles per second. The higher the tone, the higher the Hz, the faster the frequency, the more cycles per second. A cycle is the time between each tap of the plunger 71 against the diaphragm 15. So a tone of 100 Hz, which is the tone of a typical male voice, means 100 cycles per second. The human ear can hear tones from about 20 Hz to about 20,000 Hz, but the human voice operates in a range of between 80 Hz to about 250 Hz. The microcontroller 45 and transducer 70 are capable of exceeding this range but the representative example used herein has limited this range from a 40 Hz minimum frequency to a 180 Hz maximum frequency. This is because, in part, frequencies at the highest vibratory tones do not always transmit through the neck in a manner best suited to quality speech generation. Tone is a measure of sound, but tone is a function of the speed of the transducer 70, which is its frequency.

The housing 11 is a handheld component having an overall length of about four to five inches measured along the central axis of elongation 12. The dimension can vary somewhat, though it must remain small enough to hold easily in the hand and fit against the neck and under the throat. The housing 11 can be made of molded plastic or a variety of metals or metal alloys, much like a small, hand held flashlight. In one embodiment, the housing 11 consists of a first longitudinally extending section (i.e., a first half) and a second longitudinally extending section (i.e., a second half) that are held together by the bottom and top end caps 13 and 14 to create the fully assembled housing. The top end cap 14 and bottom end cap 13 both have threaded engagement sections to allow them to be easily attached to the central housing component, and also allow easy opening to access the components within.

With the first and second sections fully assembled, the housing 11 defines a hollow interior that provides space for the components of the electrolarynx 10. The transducer 70 and its related components sits within the space at the top, substantially within the top end cap 14. The power supply 23 sits within the space at the bottom, substantially within the bottom end cap 13. Typically the power supply 23 is a standard battery or battery pack. In the preferred embodiment the power supply 23 is a standard 9 volt battery. The circuit board 40 and controlling circuitry sits in the space between the power supply 23 and the transducer 70. The circuit board 40 is connected to the power source 23 by connectors 22, and connected to the transducer 70 by wires.

Circuitry on or connected to the circuit board 40 includes the programmable microcontroller 45, a momentary electronic switch 21 with red and green LED lights 24, a multi-function thumbwheel encoder 50, and a voice coil style transducer 70. To operate the electrolarynx 10, the user depresses a pushbutton 20, which is attached to the electronic switch 21, to turn on power to the electrolarynx 10 so that the voice coil style electro-magnetic transducer 70 begins to vibrate, and the attached plunger 71 beats against a button-like diaphragm 15 creating the vibrating tone of the electrolarynx 10. When the user removes pressure from the pushbutton 20, typically be removing the finger, the vibration stops, but as described more fully below, the electrolarynx 10 does not stop completely.

Volume level of the electrolarynx 10 is selected by turning the thumbwheel 51 and controlled by the microcontroller 45. Most commonly a decrease in volume is accomplished by decreasing the amount of power and thus the magnetic force, supplied to the transducer 70 during each cycle. This results in a shorter travel of the plunger 71, and lighter strike against the diaphragm 15, if the remaining travel is such that the plunger 71 can still reach the diaphragm 15. As a result the top end cap must be adjusted such that the button-like diaphragm 15 comes closer to the plunger 71. This adjustment is accomplished by screwing the top end cap 14 further onto the middle-housing section 11 of the electrolarynx 10. In one embodiment the present invention adjusts the volume by altering the "ON-time" of the transducer 70. Each frequency cycle of the transducer includes an ON-time when the transducer 70 is activated and an OFF-time when power is not supplied to the transducer 70. The total of the ON-time plus OFF-time is equal to one cycle. In one embodiment the microcontroller 45 adjusts the ON-time of the transducer 70 rather than the power level. By maintaining the same power level at lower volumes the strength of the magnetic field remains the same, though for a shorter period of time. As a result, lower volume levels are able to be achieved without requiring the adjustment of the top end cap 14 in relation to the button-like diaphragm 15.

There is a thumbwheel style quadrature encoder 50, with a selector switch that is used for selecting volume and frequency level of the electrolarynx 10. A jog shuttle encoder could also be used in selecting adjustment modes and making tone/volume selections. The thumbwheel encoder 50 is shown in FIG. 4. The encoder 50 includes a thumbwheel 51 that is turned to adjust the volume or the tone up or down. This is achieved by the activation of two directional switches found within the encoder. A portion of the thumbwheel 51 extends out of the housing 11 as seen in FIG. 1, which allows it to be manipulated by the user. The encoder 50 is mounted on the circuit board 40 and thereby connected to the microcontroller 45. An internal program within the microcontroller 45 allows the physical movement of the thumbwheel 51 to be decoded to generate up/down counts. The counts are summed separately for Volume and Frequency levels, and those levels are saved in memory. When the thumbwheel 51 is pressed towards the rear portion 52 the selector switch within the encoder 50 is activated. The microcontroller 45 uses the activation of these switches within the multi-function thumbwheel encoder 50 as user input. In default mode, the microcontroller 45 uses turns of the thumbwheel 51 to determine the volume level of the vibrating tone of the electrolarynx 10. The volume range consists of a minimum and maximum volume level as well as a fixed number of steps from the minimum volume level to the maximum volume level. These steps are spaced such that each step is the same percentage change in volume level. As there are no stops on the thumbwheel 51, the microcontroller 45 activates a stutter sound of two fast buzzes whenever the thumbwheel 51 is turned past the top of the volume range. There is no need for an audible warning at the bottom of the volume range since the absence of sound will suffice as an indicator. When the portion of the thumbwheel 51 extending to the outside of the housing 11 is pressed by the user, the microcontroller 45 switches to a tone-change mode where the base frequency may be adjusted by rotating the thumbwheel 51.

The microcontroller 45 provides visual feedback to the user through the use of red and green LED lights 24 on the momentary electronic switch 21, which is visible to the user through a clear lens on the pushbutton 20. The LED lights 24 are wired in anti-parallel and the microcontroller 45 controls the color (red or green) of the LED lights 24 by the direction of electrical current. These LED lights shine through a transparent lens on the outside surface of the pushbutton 20. The pulsing green LED light 24 indicates that the electrolarynx 10 is operating in normal mode. The red blinking LED light 24 indicates that thumb-wheel 51 has been pressed and the system is now in tone-change mode. Intensity (brightness) of the LED lights 24 is determined by the duration of time the LED Lights 24 are powered on or off in a given cycle. When the amount of on-time in an on/off cycle is varied, the user will see a pulsing glow.

The microcontroller 45 also provides audible feedback to the user through the use of musical tones generated by the vibration of the transducer 70. One audible feedback is the low battery warning tone, which the microcontroller 45 activates when it has detected a low battery power source 23. The musical tune is generated through controlled vibrations of the transducer 70. The impact rate of the plunger on the button-like diaphragm 15 is rapidly varied over a sequence of frequencies corresponding to musical notes. These musical notes are not helpful in generating the vibrating tones used to create speech but provide a audible indicator to the user which is perceived as a musical tune.

The microcontroller 45 controls all of the functions of the electrolarynx. The microcontroller is a standard controller computer chip that controls the various functions of the electrolarynx 10. As noted above, one component of the microcontroller 45 controls the LED light 24 based on the function selected by the thumbwheel encoder 50. The microcontroller 45 is programmable to control the frequency of the transducer 70 as described below. The unique feature of the present invention is the automatically varying frequency which moves in a random but controlled band, resulting in a vibrating tone that is neither monotone nor erratic or uncontrolled. Features programmed into the microcontroller 45 cause the frequency to moves around a selected base frequency in a random walk 110 as shown in FIG. 9. Each cycle time is slightly different from the last. These cycle times are based on the prior frequency cycle but include a decay factor multiplied to previous cycle time variation plus an additional random variation. This prevents wide variation between adjacent frequency points 100 while still allowing for a greater overall frequency range then would be possible with purely random fluctuations 100 modeled in graph FIG. 8.

Figure 6:
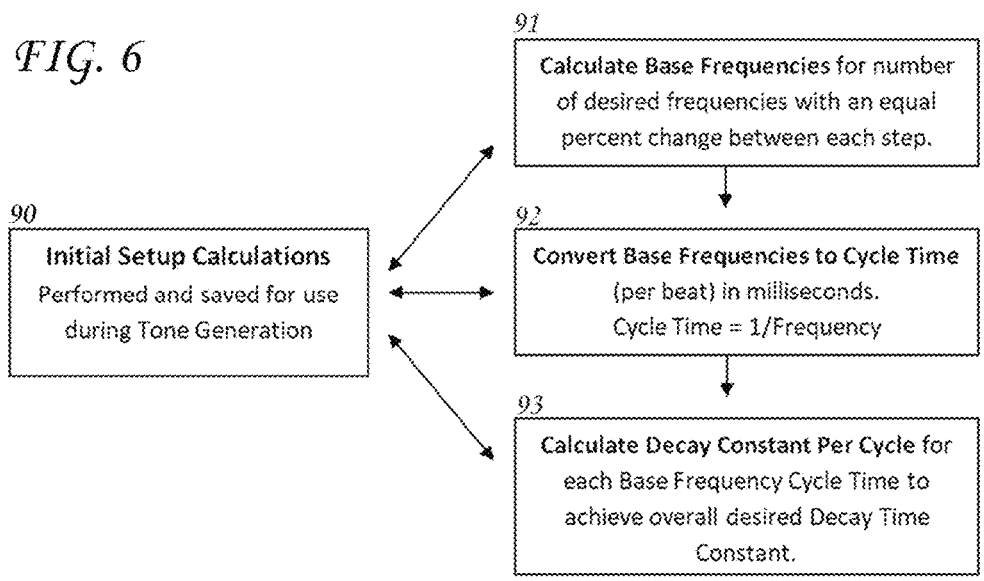
FIG. 6 is a flow chart of the initial setup calculations of the microcontroller.
Figure 7:
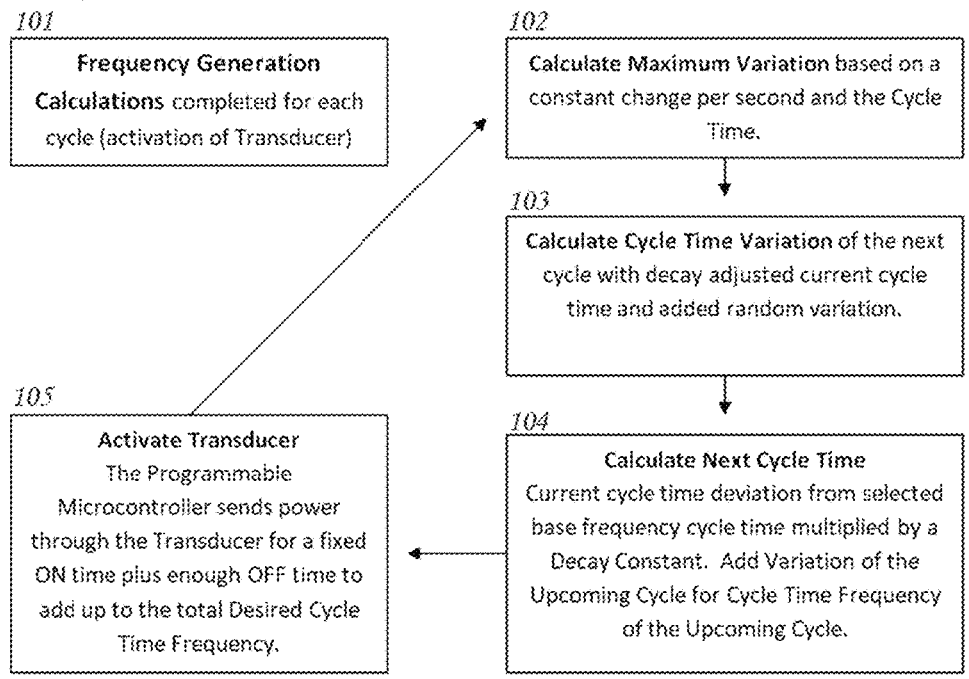
FIG. 7 is a flow chart of the tone generation mode of the microcontroller.

FIG. 5 is a flow chart of the operations of the transducer 70. FIG. 6 is a flow chart of the initial set-up of the tone generation. FIG. 7 is a flow chart of the frequency generation calculations. In order to understand the invention, the following definitions are provided:

Base Frequency: A selectable frequency 110 [i] upon which all random frequency variation is centered.
Cycle: Each combined activation and deactivation of the transducer 70, which correlates to one strike of the plunger 71 against the diaphragm 15.
Cycle Time: The combined length of ON-time and OFF-time in one cycle. 1/frequency=Cycle Time.
Decay: A programmed feature within the frequency generating program whereby any previously generated variation in frequency or cycle time is reduced during each cycle. This causes a curve of the frequency cycles to move around the base frequency.
Frequency: Number of cycles in one second. 1/Cycle Time=frequency.
Frequency Step: Numerical position of each increase in selectable frequencies.
Vibrating Tone: The perceived sound of a steady or closely related frequency. In the electrolarynx 10 the vibrating tone is the result of the plunger 71 hitting the diaphragm 15.
Variation: The amount of deviation of a cycle time from the cycle time of the base frequency.
Variation in cycle time=(cycle time)−(base frequency cycle time).

FIG. 8 is a graph showing random frequency generation confined by upper and lower frequency limits. Using this method each individual frequency cycle 110 is produced independently of other proceeding or following frequency cycles 110. The only restriction on a given frequency cycle 110 is that the frequency cycles 110 bounce somewhere around a base frequency 111 bounded by an upper frequency limit 112 and lower frequency limit 113. A line 115 has been drawn between each adjacent frequency cycle 110 to show the erratic nature of these unconnected frequency cycles 110. This type of random frequency generation is restricted to very small frequency ranges as larger ranges would sound unnatural in normal human speech. It is useful in creating static vocal sounds such as whispering.

FIG. 9 is a graph which shows a drifting random frequency as described by this invention. In this case, each frequency cycle 110 is calculated by the frequency cycle 110 which preceded it. At each cycle 110 a calculation is made for the value of the next frequency cycle 110. These calculations are set out in detail below. This calculation is based on the variation of the current frequency cycle 110 from a selected base frequency 111. This variation from the base frequency is reduced by a decay factor resulting in a decayed frequency cycle 114. A small random number is generated and added to the value of this decayed frequency cycle 114 to determine the value of the next frequency cycle 110. Frequency cycles 110 calculated in this manner are restricted to a drifting band restricted by smaller individual variation limits but an overall greater frequency range than is possible with purely randomly produced frequency cycles 110 in FIG. 8. As shown, the movement in line 115 between connected frequencies cycle 110 points in FIG. 9 results in smoother movements in the production of multiple frequency cycles 110. This results in frequency fluctuations that more closely mimic the human voice.

FIG. 5 shows a flowchart diagram of the major functions and controls described above. In the dormant mode 80 the electrolarynx circuit, including microcontroller 45, is inactive using no energy and performing no functions. When the switch-activating pushbutton 20 is pressed for a minimum of one-half second, electrolarynx circuit activation 81 begins and electricity from the power supply 23 powers the microcontroller 45.

On startup, the microcontroller 45 immediately performs and saves initial setup calculations 90 to be used during frequency generation 100. The start-up calculations 90 are set out in the flow chart of FIG. 6. These setup calculations 90 begin to calculate base frequencies based on the range of the minimum and maximum base frequencies, and the number of steps between these frequencies. A frequency step is a change in frequency. All frequency steps are calculated to be equal in the percentage of frequency increase. Next the microcontroller 45 will calculate cycle time 92 for each base frequency. Cycle time is equal to each individual activation of the transducer 70 followed by a transducer 70 off-time. Cycle time=1/Frequency. The final procedure during setup calculations 90 is to calculate the decay constant 93 for each base frequency. This constant is used to reduce any buildup in cycle time variation that would occur over time, such that the cycle times (and frequency) tends to fluctuate smoothly around the base frequency.

Once the initial setup calculations 24 have been performed the microcontroller 45 will perform a voltage check 82 of the power source 23. If the voltage check 82 shows voltage above minimum 83 the microcontroller 45 powers the LED light 24 on the momentary electronic switch 21 to begin blinking green. If the voltage check 82 shows power supply 23 voltage below minimum 83 the microcontroller 45 powers the LED light 24 on the momentary electronic switch 21 to begin blinking red and cause the transducer 70 to play a musical tune indicating a low battery warning to the user, as described above.

After determining the power source 23 voltage level, the microcontroller 45 will enter tone generation 100 mode. The light 24 on the momentary electronic switch 21 will continue to blink or pulse as determined by the voltage check 82. The user activates the electrolarynx 10 by pressing and holding down on the push button 20 which activates the transducer 70 to produce a buzzing tone based on the base frequency 91 determined in the initial setup calculation 90. The microcontroller 45 will also produce a random tone change which will minimize the robotic monotone of the standard transducer and mimics the natural variation that occurs in human speech.

Referring to the graph in FIG. 9, during tone generation 100 the microcontroller 45 will generate a tone that varies in a random pattern confined within a fixed but drifting range. A minimum and maximum frequency range is pre-programmed into the microcontroller 45. At startup the microcontroller calculates the available frequencies and the thumbwheel 51 is used to select the preferred frequency. The chosen frequency of the beating plunger 71 passes through the diaphragm 15 such that the electrolarynx 10 creates a vibrating tone that may be used to generate speech by the user.

The following terms are used in the mathematical equations during initial startup calculations 90 and frequency generation calculations 101.

Definitions and Variables

CurrentCycleTime: The actual cycle time of the current cycle.
CycleTime[i]: Cycle time of a selectable base frequency at frequency step [i]
CycleTimeNext: Cycle time for the next cycle.
DecayConst: The amount of decay on each cycle such that after a total of time of Tdecay, the original variation will have decreased by 63%. Expressed as a decimal portion of a second.
deltaF: The total variation of the current cycle from the base CycleTime[i].
deltaFnext: The total variation in the next cycle. DeltaF is also the variation of the current cycle from CycleTime[i] reduced by the DecayConst, plus the new random variation (RandFvar).
DeltaPerSec: Frequency independent constant governing the maximum amount of frequency variation. DeltaPerSec is divided by cycles per second to get the maximum variation for each cycle (Fvar).
FreqRatio: Ratio of maximum frequency to minimum frequency.
Frequency[i]: The frequency at step [i] expressed in the number of cycles per second.
Fvar: The maximum time variation to be added to the current cycle time, after decay adjustment, in calculating the next cycle time. Fvar establishes the absolute value limits within which the randomly generated variation of the next cycle must fall.
[i]: The number of steps a base frequency is above the MinFreq.
MaxFreq: Maximum Base Frequency of the electrolarynx 10.
MaxSteps: The total number of frequency steps
MinFreq: Minimum Base Frequency of the electrolarynx 10.
NumVals: Total number of frequency selections. MaxFreq–Maximum number of equal percentage steps between MinFreq and MaxFreq.
RandFvar: A randomly generated number between +TimeFvar and –TimeFvar. To be added to the decay adjusted current cycle time, thus changing the cycle time and overall frequency.
StepSize: The distance between consecutive selectable frequency levels expressed in milliseconds (1/1,000 of a second) or microseconds (1/1,000,000 of a second).
Tdecay: A constant for decay time expressing how quickly the variation in frequency of a cycle decays back to the base frequency.
TimeFvar: A conversion of Fvar from a fraction to a cycle time.

Programmed Constants
MinFreq=40
MaxFreq=180
NumVals=11
Tdecay=0.2
DeltaPerSec=1
e=2.71828

Example Equation Variables
[i]=5
RandFVar=+0.00050
CurrentCycleTime=0.012000

The Initial Setup Calculations 90 are performed at startup and saved for use during frequency generation 100. These calculations are performed and saved for each possible Frequency [i]. Calculations are later referenced during the Frequency Generation Calculations 101 so that they do not need to be calculated during each cycle. An example follows each formula where the calculations for [i]=5 are performed.

Frequency generation in the microcontroller 45 specifies a fixed frequency range and a fixed number of steps within that range. Each of the base frequencies 91 is calculated such that there is an equal percentage increase in each step between MinFreq and MaxFreq. The size of each step increases with each increase in frequency. The following equations show the calculation of the base frequency.

$$\text{FreqRatio} = \text{MaxFreq}/\text{MinFreq} \qquad 1.$$

$$\text{Example: } 180/40 = 4.5$$

$$\text{MaxSteps} = \text{NumVals} - 1 \qquad 2.$$

$$\text{Example: } 11 - 1 = 10$$

$$\text{StepSize} = (\text{FreqRatio}^{\wedge}(1/(\text{MaxFreq}))) \qquad 3.$$

$$\text{Example: } 4.5^{\wedge}(1/10) = 1.162$$

$$\text{Frequency}[i] = (\text{MinFreq}) * (\text{StepSize}^{\wedge}[i]) \qquad 4.$$

$$\text{Example: } (40 * 1.162^{\wedge}5) = 84.7$$

The next step is to convert frequency to a cycle time 92 in microseconds, as shown by the following equation:

$$CycleTime[i]=(10^{\wedge}6)*(1/Frequency[i]) \qquad 5.$$

Example: $(1,000,000)*(1/84.7)=11,806$ microseconds

The next step is to Calculate DecayConst in order to achieve the desired time decay constant Tdecay. This factor is used to reduce accumulated frequency variation from the base frequency[i] in the calculation of each following cycle. Calculation of DecayConst is shown in the following equation:

$$DecayConst[i]e^{\wedge}(-1(Tdecay*MinFreq*StepSize^{\wedge}[i])) \qquad 6.$$

Example: $(2.71828^{\wedge}(-14.2*84.7))=0.942$

The Frequency Generation Calculations 101, as shown in FIG. 7, are performed during each cycle for the next subsequent cycle. Each time the transducer 70 is activated and the plunger 71 hits the diaphragm 15 a new calculation for the next cycle time is calculated. Frequency calculations for the next cycle are based on the variation from CycleTime[i] of the current cycle time. Fvar is reduced by a decay constant (DecayConst) and the result is added to a randomly generated variation for the next cycle (deltaF). This results in constantly shifting cycle times that move in a closely related band drifting above and below the CycleTime[i] of the base Frequency[i], as shown in FIG. 9.

The first step is to calculate the maximum variation of the next cycle time, expressed as a decimal fraction, Fvar, as shown in the following equation:

$$Fvar=CycleTime[i]*DeltaPerSec*(10^{\wedge}-6) \qquad 7.$$

Example: $11,806*1*(10^{\wedge}-6)=0.011806$

The next step is to calculate time variation of next cycle 103 from CycleTime[i], as shown in the following equation:

$$TimeFvar=(Fvar)*(CycleTime) \qquad 8.$$

Example: $011806*0.011806=0.000139$ seconds

The next step is to generate a random number (RandFvar) to be added to additional next cycle variation such that the number falls between negative and positive TimeFvar. The result shown below is for RandFvar=+0.00050, in the following equation:

$$RandFvar=random\ number([-TimeFvar,+TimeFvar]) \qquad 9.$$

Example: RandFvar=random number([−0.00139,+0.00139]): RandFvar=+0.00050

The next step is to calculate the next cycle time 104 based on the variation of the current cycle (deltaF), the decay constant DecayConst[i] and the random variable RandFvar. The result will be close to but different from the current cycle time. This is accomplished by the following series of equations:

$$deltaF=(CurrentCycleTime)-(CycleTime[i]) \qquad 10.$$

Example: $0.012000-0.011806=0.000194$ $$deltaFnext=(DecayConst[i])*(deltaF)+(RandFvar) \qquad 11.$$

Example: $0.942*0.000194+0.00050=0.000183+0.00050=0.000683$ $$CycleTimeNext=(CycleTime[i])+FvarNext \qquad 12.$$

Example: $0.011806+0.00068=0.012486$

The final step is to Activate Transducer 105 such that the cycle time will be 0.012486 second with a frequency of 1/0.012486=80.09 beats/second. Proceed to Calculate Maximum Variation 102 for the next cycle and repeat tone generation calculations 101. FIG. 9 graphically depicts this.

When the user is ready to end frequency generation 100, the switch 21 may be deactivated by removing pressure from the pushbutton 20. The thumbwheel 51 on the encoder 20 may be turned for volume level change 88 either regardless of whether the switch 21 is activated. When pressure on the pushbutton 20 is released and switch deactivated 85, frequency generation 100 will cease but the light 24 will continue to blink or pulse as determined during voltage check 82. The user may choose to enter volume level change 87, enter base frequency change 87, or leave the electrolarynx 10 functions untouched and inactive for one minute, causing the electrolarynx 10 to enter shut-down-mode.

Pressing on the outside of the thumbwheel of the multi-function thumbwheel encoder 20 activates change base-tone 87. A solid red light 24 in the momentary electronic switch 16 will come on and the transducer 18 will be activated to produce the base frequency of the electrolarynx. The thumbwheel of the multi-function thumbwheel encoder 20 is rotated causing the base tone to change. Change base tone 87 mode may be exited and a new selected base frequency saved by pressing the switch-activating pushbutton 16.

If the switch is inactive for one minute 32 the microcontroller 45 will cease to draw power and will switch the volume selection to memory and enter dormant mode 80, the microcontroller 45 will allow the connection to the power source to shut down, LED lights 24 will stop blinking and all functions of the microcontroller 45 and electrolarynx 10 will cease.

The present invention is well adapted to carry out the objectives and attain both the ends and the advantages mentioned, as well as other benefits inherent therein. While the present invention has been depicted, described, and is defined by reference to particular embodiments of the invention, such reference does not imply a limitation to the invention, and no such limitation is to be inferred. The depicted and described embodiments of the invention are exemplary only, and are not exhaustive of the scope of the invention. Consequently, the present invention is intended to be limited only be the spirit and scope of the claims, giving full cognizance to equivalents in all respects.

We claim:

1. An automatic variable frequency electrolarynx comprising:
    a housing, having a transducer, a power source to power said transducer, and control circuitry to control the transducer, disposed therein;
    said control circuitry including a power button, an encoder, and a microcontroller;
    wherein said transducer produces a vibration at a specified frequency;
    wherein said microcontroller controls the frequency of the vibration and hence the tone of the transducer;
    wherein said microcontroller also creates a random variation in the frequency to create a tone to mimic the natural variations in human speech
    wherein said microcontroller creates a base frequency and wherein said random variation in frequency drift but are constrained within a range around said base frequency, and wherein said random variation in frequency allows the frequency to gradually, but constantly wander around said base frequency, and thereby allows the tone of the transducer to wander around said base tone.

2. The automatic variable frequency electrolarynx of claim 1 wherein said random variation is calculated from a current cycle.

3. The automatic variable frequency electrolarynx of claim 2 wherein said random variation in frequency increases as the frequency of the vibration increases.

4. The automatic variable frequency electrolarynx of claim 3 wherein the random variation includes a decay constant that returns the frequency back towards the base frequency.

5. The automatic variable frequency electrolarynx of claim 3 wherein the random variation is calculated from said current cycle, and wherein said variation from said base frequency is multiplied by said decay factor to prevent variation build-up over time.

6. The automatic variable frequency electrolarynx of claim 1 wherein said encoder is a multi-function encoder that provides an input to said microcontroller to manually control the volume or select the frequency of the transducer which controls the tone of the electrolarynx.

7. The automatic variable frequency electrolarynx of claim 6 wherein said multi-function encoder includes:
a thumbwheel, and a selector switch that allows a user to select between a first function and a second function; and
wherein in said first function said thumbwheel controls the volume, and in said second function said thumbwheel controls the frequency.

8. The automatic variable frequency electrolarynx of claim 7 wherein said thumbwheel is a digital encoder having no top or bottom range stop, and wherein said microcontroller generates a tone stutter to indicate that the thumbwheel has reached a top volume range.

9. The automatic variable frequency electrolarynx of claim 6 wherein said microcontroller generates a transducer on-time to activate the transducer, and wherein said volume control is achieved by increasing or decreasing said transducer on-time.

10. The automatic variable frequency electrolarynx of claim 7 further including:
an LED light attached to said control circuitry and said microcontroller, said LED light capable of producing red or green light;
a clear window on said power button, wherein said LED light is visible through said clear window;
wherein said LED light provides visual information to the user regarding the operation of said electrolarynx.

11. The automatic variable frequency electrolarynx of claim 10 wherein said LED light illuminates green when in said first function to control the volume, and illuminates red when in said second function to control the frequency.

12. The automatic variable frequency electrolarynx of claim 1 wherein said microcontroller performs an initial power source voltage check, and wherein further if said initial power source voltage check indicates that said power source voltage is below a pre-determined minimum level said microcontroller will generate a preset frequency pattern to create a musical tone as a low battery warning.

13. The automatic variable frequency electrolarynx of claim 4 wherein said microcontroller performs an initial setup calculation to determine the base frequency, a maximum frequency variance for each base frequency, and the decay constant.

14. The automatic variable frequency electrolarynx of claim 13 wherein the microcontroller generates an initial frequency cycle based on the base frequency and the frequency variance, and then generates a subsequent frequency cycle based on said initial frequency cycle, said frequency variance, and said decay constant; and wherein each subsequent frequency cycle is based on the previous frequency cycle factored by said frequency variance and said decay constant; thereby producing the random variation in the frequency to create a tone to mimic the natural variations in human speech.

15. An electrolarynx comprising:
a housing, having a transducer, a power source to power said transducer, and control circuitry to control the transducer, disposed therein;
said control circuitry including a power button, an LED light, an encoder with a selector switch, and a microcontroller;
wherein said LED light provides visual information regarding the operation of the electrolarynx;
wherein said encoder includes a thumbwheel, and a selector switch that allows a user to select between a first function and a second function, and wherein in said first function said thumbwheel controls the volume of the electrolarynx and in said second function said thumbwheel controls the frequency of the transducer and hence the tone of the electrolarynx;
wherein said transducer produces a vibration at a specified frequency;
wherein said microcontroller controls the frequency of the vibration and hence the tone of the transducer; and
wherein said microcontroller also creates a random variation in the frequency to create a tone to mimic the natural variations in human speech.

16. The electrolarynx of claim 15 wherein said thumbwheel is a digital encoder having no top or bottom range stop, and wherein said microcontroller generates a tone stutter to indicate that the thumbwheel has reached a top volume range.

17. The electrolarynx of claim 15 wherein said microcontroller creates a base frequency and wherein said random variation is calculated from a current cycle;
wherein the random variation includes a decay constant that returns the frequency back towards the base frequency, which allows the frequency to gradually, but constantly wander around said based frequency, and thereby allows the tone of the transducer to wander around said base tone.

18. An electrolarynx comprising:
a housing, having a transducer, a power source to power said transducer, and control circuitry to control the transducer, disposed therein;
said control circuitry including a power button, a multi-function encoder, and a microcontroller;
wherein said transducer produces a vibration at a specified frequency;
wherein said microcontroller controls the frequency of the vibration and hence the tone of the transducer;
wherein said microcontroller performs an initial setup calculation to determine a base frequency, a maximum frequency variance for each base frequency, and a decay constant that returns the frequency back towards the base frequency;
wherein the microcontroller generates an initial frequency cycle based on the base frequency and the frequency variance, and then generates a subsequent frequency cycle based on said initial frequency cycle, said frequency variance, and said delay constant; and wherein each subsequent frequency cycle is based on the previous frequency cycle factored by said frequency variance and said delay constant; thereby producing the random variation in the frequency to create a tone to mimic the natural variations in human speech.

19. The electrolarynx of claim 18 wherein said multi-function encoder provides an input to said microcontroller to manually control the volume and the frequency of the transducer which controls the tone of the electrolarynx.

20. The electrolarynx of claim 19 wherein said multi-function encoder includes:
a thumbwheel, and a selector switch that allows a user to select between a first function and a second function; and
wherein in said first function said thumbwheel controls the volume, and in said second function said thumbwheel controls the frequency.

21. The electrolarynx of claim 20 wherein said thumbwheel is a digital encoder having no top or bottom range stop, and wherein said microcontroller generates a tone stutter to indicate that the thumbwheel has reached a top volume range.

22. The electrolarynx of claim 21 further including:
an LED light attached to said control circuitry and said microcontroller, said LED light capable of producing red or green light;
a clear window on said power button, wherein said LED light is visible through said clear window;
wherein said LED light provides visual information to the user regarding the operation of said electrolarynx.

23. The electrolarynx of claim 22 wherein said LED light illuminates green when in said first function to control the volume, and illuminates red when in said second function to control the frequency.

24. The electrolarynx of claim 18 wherein said microcontroller performs an initial power source voltage check, and wherein further if said initial power source voltage check indicates that said power source voltage is below a pre-determined minimum level said microcontroller will generate a preset frequency pattern to create a musical tone as a low battery warning.

25. The automatic variable frequency electrolarynx of claim 8 wherein said microcontroller will generate a preset frequency pattern to create a musical tone as a system indicator.

26. The automatic variable frequency electrolarynx of claim 25 wherein said system warning is a low battery warning.

27. The automatic variable frequency electrolarynx of claim 7 wherein said user can select a desired based frequency to correspond to the user's natural voice tone thus allowing the device to be used by any user.

28. An automatic variable frequency electrolarynx comprising:
a housing, having a transducer, a power source to power said transducer, and control circuitry to control the transducer, disposed therein;
said control circuitry including a power button and a microcontroller;
wherein said transducer produces a vibration at a specified frequency;
wherein said microcontroller controls the frequency of the vibration and hence the tone of the transducer;
wherein said microcontroller also creates a random variation in the frequency to create a tone to mimic the natural variations in human speech; and
wherein said microcontroller creates a base frequency and wherein said random variation in frequency drift but are constrained within a range around said base frequency, and wherein said random variation in frequency allows the frequency to gradually, but constantly wander around said base frequency, and thereby allows the tone of the transducer to wander around said base tone.

29. The automatic variable frequency electrolarynx of claim 28 wherein said random variation is calculated from a current cycle.

30. The automatic variable frequency electrolarynx of claim 28 wherein said random variation in frequency increases as the frequency of the vibration increases.

31. The automatic variable frequency electrolarynx of claim 28 wherein the random variation includes a decay constant that returns the frequency back towards the base frequency.

32. The automatic variable frequency electrolarynx of claim 28 wherein the random variation is calculated from said current cycle, and wherein said variation from said base frequency is multiplied by said decay factor to prevent variation build-up over time.

33. The automatic variable frequency electrolarynx of claim 28 wherein said microcontroller performs an initial power source voltage check, and wherein further if said initial power source voltage check indicates that said power source voltage is below a pre-determined minimum level said microcontroller will generate a preset frequency pattern to create a musical tone as a low battery warning.

34. The automatic variable frequency electrolarynx of claim 28 wherein said microcontroller performs an initial setup calculation to determine the base frequency, a maximum frequency variance for each base frequency, and the decay constant.

35. The automatic variable frequency electrolarynx of claim 34 wherein the microcontroller generates an initial frequency cycle based on the base frequency and the frequency variance, and then generates a subsequent frequency cycle based on said initial frequency cycle, said frequency variance, and said decay constant; and wherein each subsequent frequency cycle is based on the previous frequency cycle factored by said frequency variance and said decay constant; thereby producing the random variation in the frequency to create a tone to mimic the natural variations in human speech.

* * * * *